United States Patent
Tomczak

(10) Patent No.: US 6,719,965 B2
(45) Date of Patent: Apr. 13, 2004

(54) ANTIPERSPIRANT OR DEODORANT COMPOSITION

(75) Inventor: Douglas Charles Tomczak, Evanston, IL (US)

(73) Assignee: Unilever Home & Personal Care USA division of Conopco, Inc., Chicago, IL (US)

(*) Notice: Subject to any disclaimer, the term of this patent is extended or adjusted under 35 U.S.C. 154(b) by 25 days.

(21) Appl. No.: 10/078,880

(22) Filed: Feb. 19, 2002

(65) Prior Publication Data

US 2003/0157044 A1 Aug. 21, 2003

(51) Int. Cl.⁷ .............................. A61K 7/32; A61K 7/00
(52) U.S. Cl. ......................... 424/65; 424/400; 424/401
(58) Field of Search ............................ 424/65, 400, 401

(56) References Cited

U.S. PATENT DOCUMENTS

| 6,074,632 A | 6/2000 | Shen | 424/65 |
| 6,126,928 A | 10/2000 | Swaile | 424/65 |
| 6,149,897 A | 11/2000 | Swaile | 424/65 |
| 6,399,049 B1 * | 6/2002 | Swaile et al. | 424/65 |

FOREIGN PATENT DOCUMENTS

WO 01/56539 8/2001

* cited by examiner

Primary Examiner—Shelley A. Dodson
(74) Attorney, Agent, or Firm—Kevin J. Stein

(57) ABSTRACT

An antiperspirant/deodorant composition comprising a polyol associated with a particulate antiperspirant/deodorant active prior to mixing with other components of the antiperspirant/deodorant composition. The resulting composition provides numerous benefits including aesthetic, processing and thermal stability.

20 Claims, No Drawings

ANTIPERSPIRANT OR DEODORANT COMPOSITION

FIELD OF THE INVENTION

The invention relates to antiperspirant and deodorant compositions, and more particularly to such compositions comprising a polyol.

BACKGROUND

Typical deodorant and antiperspirant products on the market use aluminium or aluminum-zirconium salts to prevent, or at least control, perspiration at the skin surface, particularly in the underarm, whilst often simultaneously providing a perceived degree of deodorancy.

A principal disadvantage of many antiperspirant and deodorant products is their perceived skin unfriendliness. More particularly, the presence of volatile carriers such as volatile silicones and ethanol, and indeed antiperspirant and deodorant actives is perceived to have a drying and tightening effect on the user's skin following application, resulting in dry skin, reduced skin elasticity and an unpleasant skin sensation.

Many antiperspirant and deodorants can also result in a stinging sensation on the skin following application due to the presence of astringent, skin drying materials such as ethanol and the aluminum and aluminum-zirconium underarm salts. Stinging is particularly problematic when an antiperspirant or deodorant is applied following shaving.

In order to overcome these disadvantages, moisturising creams have been incorporated into antiperspirant and deodorant compositions. For example, U.S. Pat. Nos. 5,932,199, 6,099,827, and 6,221,345 disclose antiperspirant compositions comprising moisturising cream.

Moisterising creams typically comprise numerous components such as glycerin. However, the incorporation of materials like glycerin into antiperspirant and deodorant formulations cause progressively greater difficulties as their proportion increases. Incorporation of materials like glycerin into antiperspirant and deodorant formulations requires the use of additional materials to aid in the processing. These additional materials, though, adversely affect the aesthetics of the formulation as well as other physical properties. One of the more significant problems comprises the potential of grit formation during the manufacture of the formulation, which noticeably can impair the sensory properties of the formulation. This is particularly apparent for skin which has been sensitised, for example by shaving.

Accordingly, it is an object of the present invention to provide an antiperspirant and/or deodorant composition containing a polyol that has excellent aesthetic properties.

It is a further object of the present invention to provide an antiperspirant and/or deodorant composition containing a polyol that does not require the use of additional processing materials.

It is a further object of the present invention to provide an antiperspirant and/or deodorant composition containing a polyol that does not have gritiness.

It is a further object of the present invention to provide an antiperspirant and/or deodorant composition containing a polyol that has improved thermal stability.

SUMMARY OF THE INVENTION

According to the invention there is provided an antiperspirant or deodorant composition comprising an antiperspirant/deodorant active and a polyol, wherein at least part of the polyol is associated with the antiperspirant/deodorant active prior to mixing with other ingredients of the formulation. Preferably, the polyol is glycerin.

DETAILED DESCRIPTION OF THE INVENTION

In the present invention it has been found that anhydrous suspension antiperspirant and deodorant compositions containing polyol, numerous physical benefits are gained by associating the polyol with the antiperspirant/deodorant active prior to mixing with the other ingredients of the composition. Anhydrous as used herein means compositions containing less than 10% water, and preferably less than 5% water. This water may be complexed with the antiperspirant/deodorant active salt.

The benefits gained as a result of the present invention include being easier to apply, having better glide, dispensing more evenly, feeling lighter, having better absorption, being easier to process, and having improved thermal stability.

Suitable polyols for the present invention are, without limitation, those having from 2 to 8 carbon atoms and from 2 to 8 hydroxyl groups, preferably from 3 to 6 carbons atoms; particularly at least 3 hydroxyl groups, such as from 3 to 6, and especially 3 hydroxyl groups. Specifically, suitable polyols which may be useful for the present invention include, without limitation, polyhydric aliphatic alcohols, glycerol, pentaerythritol, sorbitol, xylitol, dulcitol, mannitol, mesoerythritol, butanetriol, trimethylolpropane, adonitol, arabitol, threitol, inositol, scyllitol, iditol, 2,5-anhydro-D-mannitol, 1,6-anhydro-glucose, and hexanetriol. Preferably, the polyol is glycerin.

Preferably, the polyol associated with the antiperspirant/deodorant active is present at 0.5–20% by weight of the underarm salt composition. More preferably, the polyol associated with the underarm salt active is present at 3–12% by weight of the salt composition and even more preferably present at 6–10% by weight of the salt composition.

Furthermore, it is preferable, in antiperspirant/deodorant compositions in accordance with the present invention, for the total polyol level (of which is at least part of is associated with the antiperspirant/deodorant active prior to mixing the active with the other components) is present at 0.12–5% by weight of the antiperspirant/deodorant composition. More preferably, the total polyol level in the antiperspirant/deodorant composition is 0.75–3% by weight of the antiperspirant/deodorant composition and even more preferably present at 1.5–2.5% by weight of the antiperspirant/deodorant composition.

The particulate antiperspirant/deodorant active may be an astringent salt or an anti-microbial agent. The astringent salts may be inorganic or organic salts of aluminum, zirconium, zinc and mixtures thereof. Salts useful as astringents or as components of astringent aluminum complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y\cdot XH_2O$ where Q is chlorine, bromine or iodine, where x is 2 to 5 and x+y=6 and x and y do not need to be integers; and where X is about 1 to 6.

Several types of complexes utilizing the above astringent salts are known in the art. For example, U.S. Pat. No. 3,792,068 (Luedders et al.), discloses complexes of aluminum, zirconium and amino acids such as glycine.

Complexes reported therein and similar structures are commonly known as ZAG. The ZAG complexes ordinarily have an Al:Zr ratio of from about 1.67 to 12.5 and a Metal:Cl ratio of from about 0.73 to 1.93. The preferred amino acid for preparing such ZAG-type complexes is glycine of the formula $CH_2(NH_2)COOH$. Spherical ZAG, with particle size 1 to 100 microns, is especially preferred.

More specifically, the following is a list of antiperspirant actives which may be useful for the present invention and which have approved listings under the United States Food & Drug Administration, Federal Register. They include aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY.

Amounts of the active astringent salt may range from about 1 to about 40%, preferably from about 10 to about 35%, optimally from about 15 to about 30% by weight of the composition.

The antiperspirant salts are employed herein in particulate form and usually in compositions that are conveniently referred to as anhydrous or substantially anhydrous. As previously mentioned, anhydrous, as used herein, means compositions containing less than 10% water, and preferably less than 5% water, and more preferably less than 3% water. This water may be complexed with the antiperspirant/deodorant active salt.

The polyol containing antiperspirant/deodorant actives of the present invention preferably have a polyol to total metal salt mole ratio of less than 0.5:1. More preferably, the polyol to total metal salt mole ratio is less than 0.4:1 or 0.3:1. Even more preferably the polyol to total metal salt mole ratio is less than 0.2:1. Additionally, the polyol to total metal salt mole ratio is at least 0.01:1, preferably at least 0.05:1, and more preferably 0.1:1.

According to the present invention, at least part of the polyol component in the antiperspirant/deodorant product composition is associated with the antiperspirant/deodorant active component prior to being mixed with other components. By associated it is meant that the polyol is added into/onto the antiperspirant/deodorant active prior to mixing the antiperspirant/deodorant active with the other components of the antiperspirant or deodorant product. The polyol may be associated/added to the antiperspirant/deodorant active either during a spray drying process or added directly to the antiperspirant/deodorant active using liquid/solids processing technique.

Accordingly, in accordance with the present invention, the polyol containing antiperspirant/deodorant composition of the present invention preferably has a polyol to total metal salt mole ratio of less than 0.5:1. More preferably, the polyol to total metal salt mole ratio is less than 0.4:1 or 0.3:1. Even more preferably the polyol to total metal salt mole ratio is less than 0.2:1. Additionally, the polyol to total metal salt mole ratio in the antiperspirant/deodorant composition is at least 0.01:1, preferably at least 0.05:1, and more preferably 0.1:1.

When adding the polyol to the antiperspirant/deodorant active during a spray drying process, the polyol is added to the antiperspirant/deodorant active solution prior to spray drying. Then the solution containing the polyol and antiperspirant/deodorant active is spray dried, as is known in the art, to form a powder. This results in the polyol becoming incorporated into the antiperspirant/deodorant active solid matrix.

When the polyol is added directly to the antiperspirant/deodorant active using liquid/solids processing, a spray dried antiperspirant/deodorant active powder is mixed at high shear while the polyol is slowly added. It is important that the polyol be added slowly so as to minimize agglomeration. As higher levels of polyol are added, it may become necessary to add low levels of fumed or precipitated silica as a processing aid in order to maintain flowability of the powder. Other suitable flow aids which may be used include, without limitation, talc and starch. Even though some silica may be required in this process, it should only be needed at low levels, thus making maintaining improved aesthtic and processing benefits.

As previously mentioned, processing polyol containing antiperspirant or deodorant according to the present invention wherein the polyol is associated with the antiperspirant/deodorant active of the antiperspirant or deodorant product eliminates the need for the use of silica. In the case of adding polyol to the antiperspirant/deodorant active using liquid/solids processing, a small amount of silica may still be needed, but at a much lower level. It has been found that formulations wherein the polyol is associated with the antiperspirant/deodorant active prior to mixing with the other ingredients of the antiperspirant or deodorant formulation exhibit preferred application aesthetics compared to those wherein the polyol is not associated with the antiperspirant or deodorant active prior to mixing with the other ingredients. These aesthetic benefits are shown in Table 3.

Antiperspirant and deodorant compositions in accordance with the present invention may be made in various forms including solid sticks, soft solids, creams, roll-ons and aerosols. Compositions in accordance with the present invention will comprise a particulate antiperspirant/deodorant active, as described previously, associated with a polyol prior to mixing with the other ingredients of the composition. It is not necessary that all of the polyol component be associated with the antiperspirant/deodorant active prior to mixing with the other components. Accordingly, part of the polyol component may be associated with the antiperspirant/deodorant active prior to mixing with the other components and the remaining polyol mixed in with the other components.

The remaining components of antiperspirant and deodorant compositions comprising an active according to the present invention will be those typically associated with the various forms of topical antiperspirant and deodorant compositions including, but not limited to, carrier material, emollients, thickening/structuring agents, wash-off agents, processing aids, bulking/filler agents, perfumes and skin benefit agents. The use of such substances depends on the form of the composition.

Suitable carrier material for the antiperspirant/deodorant composition according to the present invention can comprise, without limitation, one or more of volatile carrier fluids, one or more of non-volatile emollients, and one or a combination of thickener and/or structurant materials if required. Examples include, without limitation, liquid siloxanes and particularly volatile polyorganosiloxanes, i.e. liquid materials having a measurable vapour pressure at ambient conditions. The polyorganosiloxanes can be linear or cyclic or mixtures thereof. Preferred siloxanes include polydimethsiloxanes and particularly those containing from 3 to 9 silicon atoms and preferably not more than 7 silicon atoms. Most preferred polydimethsiloxanes are cyclic containing from 4 to 6 silicon atoms, otherwise often referred to as cyclotetramethicone, cyclopentamethicone and cyclohexamethicone, and mixtures thereof.

Suitable volatile silicones can also comprise branched linear or cyclic siloxanes such as the aforementioned linear or cyclic siloxanes substituted by one or more pendant —O—Si $(CH_3)_3$ groups. Examples of commercially available silicone oils which are employable include Dow Corning 344, Dow Corning 345 and Dow Corning 244, Dow Corning 245 and Dow Corning 246, and grades of Dow Corning 200 with viscosity of below 10 centistokes (from Dow Corning Corporation) Silicone 7207 and Silicone 7158 (from Union Carbide Corporation) and SF1202 (from General Electric [US]). Volatile silicones are often present in antiperspirant/deodorant compositions in a proportion of from 10 to 90% and in many formulations from 20 to 70%.

Suitable non-volatile silicone oils include polyalkyl siloxanes, polyalkylaryl siloxanes and polyethersiloxane copolymers. These can suitably be selected from dimethicone and dimethicone copolyols. Commercially available non-volatile silicone oils include grades of Dow Corning 556 and Dow Corning 200 series having viscosities of above 20 centistokes. Non-volatile silicones are often present in not more than about 30% by weight of the composition, and preferably from 1 to 15% by weight. In many instances, when a non-volatile silicone oil is present, its weight ratio to volatile silicone oil is in the range of from 1:3 to 1:100.

Suitable non-silicone organic carriers include liquid aliphatic hydrocarbons such as mineral oils or hydrogenated polyisobutene, often selected to exhibit a low viscosity. A further example of liquid hydrocarbons comprises polydecene and liquid paraffins and isoparaffins containing at least 10 carbons. The liquid hydrocarbons are often present in a proportion of from 0 to 80%, and particularly 0 to 20% by weight.

Other suitable carriers are liquid aliphatic esters containing at least one long chain alkyl group, such as esters derivable from $C_1$–$C_{20}$ alkanols esterified with a $C_8$ to $C_{22}$ alkanoic acid or $C_6$ to $C_{10}$ alkanedioic acid. Suitable aliphatic esters include isopropyl myristate, lauryl myristate, isopropyl palmitate, diisopropyl sebacate and diisopropyl adipate, of which isopropyl palmitate is particularly favoured. Further suitable esters comprise liquid aromatic esters, including fatty alkyl benzoates having a melting point of below 20° C., such as $C_8$ to $C_{18}$ alkyl benzoates. The liquid esters are often present in a proportion of from 0 to 30% by weight.

The carrier can additionally or alternatively comprise liquid aliphatic ethers derivable from at least one fatty $C_8$ to $C_{18}$ alcohol, particularly polyglycol ethers, such as PPG-3 myristyl ether or lower alkyl ethers of polyglycols such as PPG-14 butyl ether.

Suitable propellants typically used as carriers in aerosols include, without limitation, volatile organic compounds of boiling point less than 40° C., preferably less than 20° C. and optimally no higher than 10° C. Suitable propellant classes include $C_1$–$C_6$ hydrocarbons, $C_2$–$C_8$ dialkyl ethers, carbon dioxide and halo hydrocarbons. Among the useful hydrocarbons are propane, isopropane, butane, isobutane, isopentane, pentane and mixtures thereof. Propellants are available under the mark A31 (purely isobutane) and A45 (isobutane/isopropane) from the Phillips Petroleum Company. A preferred propellant is A50 which is a blend of isobutane/propane. Another useful propellant is dimethyl ether.

In an aerosol formulation, the antiperspirant/deodorant active is diluted with a propellant such as one or more of those mentioned herein. Aerosol formulations often comprise from 40 to 99 parts by weight, and particularly 50 to 95 parts by weight propellant and the remainder being the antiperspirant base composition. Another ingredient that may, if desired, be incorporated in aerosol compositions is an anticlogging agent.

It will be recognised that when a particulate antiperspirant is employed in such hydrophobic carriers, it will form a suspension. The carrier fluid is selected according to the physical form of the cosmetic composition and can be selected by those skilled in the art to provide appropriate physical and sensory properties for the product.

Suitable emollients, if used in the composition, may consist of a single emollient compound or a mixture of emollients, and can typically include fatty acids and fatty alcohol esters, hydrocarbons, water insoluble ethers, mineral oils and polyorganosiloxanes, and mixtures thereof. The non-volatile carrier fluids described herein may also function as emollients.

The thickening or structurant agent(s), if used in the composition, is selected according to the product form of the antiperspirant/deodorant composition. It can be any of a number of compositions, including without limitation, for example, hydrogenated vegetable oil, hydrogenated castor oil, fatty acids, beeswax, paraffin wax, silicone wax, fatty alcohols, polymers such as hydroxypropylcellulose, clays such as Bentone, natural or synthetic gums, or mixtures or combinations thereof.

The structurant or structurants that are included in compositions can comprise organic structurants and/or inorganic thickeners.

Organic structurants employable herein can be non-polymeric or polymeric. Non-polymeric structurants, including waxes and gellants, are often selected from fatty acids or salts thereof, often containing from 12 to 30 carbons such as stearic acid or sodium stearate, and/or fatty alcohols (typically insoluble in water) often containing from 12 to 30 carbons such as stearyl alcohol. Fatty herein indicates a long chain aliphatic group, such as at least 8 or 12 linear carbons, which is frequently not branched (linear) and is typically saturated, but which can alternatively be branched and/or unsaturated. It is possible for the fatty acid to contain an hydroxyl group, as in 12-hydroxystearic acid, for example as part of a gellant combination, and to employ amido or ester derivatives thereof. Examples of suitable higher molecular weight alcohols include stearyl or behenyl alcohol and sterols such as lanosterol.

Suitable gellants can comprise dibenzoyl alditols, of which a preferred representative comprises dibenzoyl sorbitol. Other organic structurants can comprise hydrocarbon waxes such as paraffin waxes, microcrystalline waxes, ceresin, squalene, and polyethylene waxes (mol weight typically 200 to 10000). Other suitable structurants are waxes derived or obtained from plants or animals such as hydrogenated castor oil (castor wax), carnabau, spermacetti, candelilla, beeswax, modified beeswaxes, and Montan wax and individual waxy components thereof. Such waxes often comprise a mixture of waxy components including one or more of fatty alcohols and esters, fatty acids and esters, and hydrocarbons such as paraffins. The waxes from some plants comprise fatty ester derivatives of polyols, such as glycerol. Mono and especially di and triglycerides are often very desirable. Synthetic glycerides can be obtained in various grades of Synchrowax™. A combination of glycerides alleged to have desirable properties comprises a mixture of behenate and C18 to C40 non-behenate glycerides (20:1 to 1:1).

It is especially suitable herein to employ a wax structurant or mixture of wax structurants. Mixtures of the organic structurants can be employed, such as mixtures of a fatty acid/salt with a wax. Suitable choice of mixtures of structurants can reduce the visibility of antiperspirant/deodorant composition deposited in use on the skin. Wax structurants are typically present in an amount of from 5 to 20% by weight when present as a principal structurant and in lower amounts such as up to 6% when present in a supplementary role.

Some suitable structurants form a fibrous network, such as selected n-acyl amino acid derivatives, including ester and amide derivatives, such as N-Lauroyl-L-glutamic acid di-n-butylamide, either by itself or when contemplated in conjunction with hydroxystearic acid or an ester or amide derivative thereof. Still further gellants include amide derivatives of di or tribasic carboxylic acids, such as alkyl N,N' dialkylsuccinimides, eg dodecyl N,N'-dibutylsuccinimide.

Polymeric gellants which can be employed can comprise organo polysiloxane elastomers such as reaction products of a vinyl terminated polysiloxane and a cross linking agent or alkyl or alkyl polyoxyalkylene-terminated poly(methyl substituted) or poly(phenyl substituted) siloxanes. Other polymeric gellants can comprise polyacrylamides, optionally polysiloxane/polyamide copolymers. Polymeric structurants are often employed in an amount of from 1 to 15% by weight.

It is often convenient to employ a polymeric thickener such as ester derivatives of polysaccharides or cellulosic materials, and in particular fatty acid esters of polysaccharides such as dextrin. The fatty acids are advantageously from c12 to C18 aliphatic acids, such as palmitic acid, and the dextrin polysaccharide backbone commonly contains from 10 to 50 repeat units. Examples are commercially available under the trade name Rheopearl. Other examples of polymeric thickeners include polyamides available under the mark Versamid 950. Yet further thickeners styrene/alkylenbe block copolymers under the mark Kraton G, or styrene copolymers under the mark Kristalex. The proportion of thickening polymer is often chosen in the range of from 2 to 10%, and in many instance from 3 to 7% by weight.

Where a significant fraction of the carrier in the composition comprises a monohydric alcohol and/or a di or polyol, it can be convenient to employ as thickener, at least in part, a dibenzoyl derivative of a saccharide, and especially dibenzoyl sorbitol.

Where the composition comprises as a significant fraction of the carrier a volatile silicone, it can be preferable to employ a silicone elastomer and in particular a crosslinked polyorganosiloxane obtained by crosslinking a vinyl terminated siloxane polymer or by otherwise introducing cross linking. In operation, the particulate polyorganosiloxane absorbs the volatile silicone and is conveniently employed in a weight ratio to the volatile silicone of from 1:3 to 1:20. The elastomer is preferably used to supplement a primary structurant to obtain a beneficial combination of effects.

Inorganic thickeners are often selected from siliceous and alumino-siliceous materials including silicas and clays. Many inorganic thickeners comprise a particulate colloidal silica, usually having a small particle size, such as below 1 $\mu$m. When used as the primary thickener, it is normally present in an amount of at least 3% by weight and particularly 4 to 7% by weight. It can be used as a supplementary thickener in lower amounts such as up to 3% by weight.

Clays and silicas can also function as suspending or bulking agents. Examples of suitable silicas include fumed silicas. Suitable clays include bentonites, hectorites and colloidal magnesium aluminium silicates. Commercially available clays are available under the trademarks Veegum and Laponite. It is preferable to include montmorillonite clays which have been hydrophobically surface treated, for example by reaction with an amine. Preferred hydrophobic-treated clays are available under the Trademark Bentone (various grades)

Additional bulking agents/fillers which can be contemplated include particulate fillers including talc, sodium bicarbonate, starches, including corn starch, modified starches and mixtures thereof. The amount of such additional fillers/bulking agents is often not more than 15%, and preferably up to 10% such as 1 to 5% by weight.

Compositions often, though not always, contain at least one perfume, which normally is incorporated within an oily phase in the composition, and typically is present in an amount of from 0 to 5% w/w, and in many instances from 0.2 to 2.5% w/w. The perfume can be introduced in its natural form, i.e. normally as an oil, or it can be wholly or partially encapsulated.

Suitable skin benefit agents include components which moisturise, condition or protect the skin. Suitable skin benefit agents include moisturising components, such as, for example, emollient/oils. By emollient oil is meant a substance that softens the skin and keeps it soft by retarding the decrease of its water content and/or protects the skin. A significant proportion of skin benefit agents also are capable of providing other functions to the composition. Thus, many comprise oils which can act as carriers. Others are waxes and fatty acids or alcohols which can provide structure to an oil phase, either alone or in conjunction with other materials.

Another optional ingredient includes wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

Other ingredients can also be included in the composition of the invention and include without limitation surfactants, preservatives and coloring agents for example. These ingredients are selected according the physical and chemical form of the composition.

The above components are discussed without limitation as the components to be mixed with the antiperspirant/deodorant active associated with a polyol in accordance with the present invention are not limiting.

As previously stated, the compositions of this invention may be in any desired form including solid, soft solid, roll-on, and aerosol. Whichever form the composition takes, it can be dispensed in conventional dispensers as known in the art.

A composition of this invention will usually be marketed as a product comprising a container with a quantity of the composition therein, where the container has at least one aperture for the delivery of composition, and means for urging the composition in the container towards the delivery aperture.

For a solid or soft solid product form, the container will generally include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. The container may also include a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

For a composition of this invention is in aerosol form, the aerosol formulation is usually filled into an aerosol canister that is capable of withstanding pressures generated by the formulation, employing conventional filling apparatus and conditions. The canister can conveniently be a metal canister commercially available fitted with a dip tube, valve and spray nozzle through which the formulation is dispensed.

The following examples will more fully illustrate the embodiments of the present invention. All parts, percentages and proportions referred to herein and in the appended claims are by weight of the composition unless otherwise indicated.

While particular embodiments of the present invention are illustrated and described, it will be obvious to those skilled in the art that various changes and modifications can be made without departing from the spirit and scope of the present invention, and it is intended to cover in the appended claims all such modifications that are within the scope of this invention.

EXAMPLES 1–10

A set of antiperspirant/deodorant salt active compositions having an associated polyol according to the present invention are outlined in Table 1. Percentages in Table 1 represent percent of the salt composition by weight with the balance being hydroxyls.

| Example | % Glycerin | % H2O | % Al | % Zr | % Cl | % Glycine | Mole ratio Glycerine/ Al + Zr |
|---|---|---|---|---|---|---|---|
| 1 | 7.8% | 3.4% | 15.0% | 14.0% | 16.7% | 9.3% | 0.12 |
| 2 | 19.2% | 2.4% | 9.9% | 9.2% | 15.0% | 9.8% | 0.45 |
| 3 | 7.6% | 2.9% | 11.7% | 11.8% | 16.6% | 10.5% | 0.15 |
| 4 | 7.6% | 2.9% | 11.7% | 11.8% | 16.6% | 10.5% | 0.15 |
| 5 | 8.5% | 2.7% | 12.0% | 12.2% | 16.7% | 10.2% | 0.16 |
| 6 | 6.7% | 3.1% | 12.5% | 11.4% | 17.0% | 10.3% | 0.12 |
| 7 | 6.8% | 5.8% | 10.9% | 11.5% | 17.3% | 10.2% | 0.14 |
| 8 | 6.7% | 6.8% | 11.7% | 11.4% | 17.1% | 10.0% | 0.13 |
| 9 | 7.6% | 6.8% | 12.4% | 11.8% | 17.2% | 9.7% | 0.14 |
| 10 | 7.7% | 6.6% | 11.4% | 11.7% | 17.2% | 9.8% | 0.15 |

EXAMPLES 11 AND 12

Table 2 contains formulations for solid antiperspirant stick examples. The polyol component (i.e. glycerin) in Comparative Example 11 was not associated with the antiperspirant active prior to processing with the other ingredients. As a result, two percent silica was needed to aid in processing.

Example 12 was made in accordance with the present invention. In this example, the polyol component (i.e. glycerin) was associated with the antiperspirant active prior to mixing with the other ingredients of the stick formulation.

The same materials were used for comparative example 11 and example 12 with the exception that silica was used as a processing aid in comparative example 11. The absence of silica in the example 12 in accordance with the present invention further exemplifies the processing benefit of the present invention. The use of silica as a processing aid in comparative example 11 requires high shear during mixing. By associating the polyol component (or at least part of the polyol component) with the antiperspirant/deodorant active prior to mixing with the other components of the composition, a processing aid is not needed (or at least lower levels are needed), thus high shear is not required during processing.

In addition to the aesthetic and processing benefits gained by associating the polyol/polyol component with the antiperspirant/deodorant active prior to mixing with the other components, it has been found that the thermal stability benefits are provided.

Comparative example 11 and example 12 were both placed in an oven for 24 hours at 50° C. Both samples were formed with a dome shaped top commonly found in antiperspirant and deodorant stick products. Upon removal from the oven after 24 hours, the full dome in comparative example 11 had collapsed, while the dome on example 12 remained intact.

TABLE 2

| INGREDIENT | Example 11 | Example 12 |
|---|---|---|
| Carrier oil | 32.15 | 34.25 |
| Emollient oil | 17.5 | 17.5 |
| Silica | 2.0 | |
| Polyol | 2.0 | |
| Structuring agent | 14.5 | 14.5 |
| Processing aid | 2.0 | 2.0 |
| Wash-off agent | 2.0 | 2.0 |
| Skin feel modifier | 2.0 | 2.5 |
| Antiperspirant active | 25.0 | |
| Antiperspirant active w/ associated glycerol | | 26.4 |
| Perfume | 0.85 | 0.85 |

Table 3 shows the results obtained from a consumer evaluation of the solid sticks in examples 11 and 12 wherein the polyol is glycerin and wherein the glycerin is not associated with the antiperspirant/deodorant active prior to mixing with the other ingredients and contains silica required for processing (comparative example 11) versus a similar solid stick wherein the glycerin is associated with the antiperspirant/deodorant active prior to mixing with the other ingredients of the antiperspirant or deodorant formulation and does not contain silica as it is not needed for processing (example 12). The results show the stick made in accordance with the present invention is easier to apply, has better glide, dispenses more evenly, feels lighter, and has better absorption into the skin.

TABLE 3

| Attribute | Example 12 | Example 11 | No difference |
|---|---|---|---|
| Easier to apply | 27 | 0 | 1 |
| Glide | 23 | 1 | 2 |
| Dispenses more evenly | 21 | 1 | 6 |
| Felt thicker | 7 | 18 | 2 |
| Absorbs into skin better | 13 | 4 | 11 |

What is claimed is:

1. An antiperspirant or deodorant composition comprising a particulate antiperspirant/deodorant active and a polyol, wherein at least part of the polyol is associated with the antiperspirant/deodorant active prior to mixing with other ingredients of the formulation.

2. An antiperspirant or deodorant composition according to claim 1 wherein the total polyol level is 0.5–20% by weight of the underarm salt composition.

3. An antiperspirant or deodorant composition according to claim 1 wherein the total polyol level is 3–12% by weight of the underarm salt composition.

4. An antiperspirant or deodorant composition according to claim 1 wherein the total polyol level is 6–10% by weight of the underarm salt composition.

5. An antiperspirant or deodorant composition according to claim 1 wherein the ratio of total polyol in the antiperspirant/deodorant composition to total metal salt mole ratio is 0.01:1–0.5:1.

6. An antiperspirant or deodorant composition according to claim 1 wherein the ratio of total polyol in the antiperspirant/deodorant composition to total metal salt mole ratio is 0.01:1–0.4:1.

7. An antiperspirant or deodorant composition according to claim 1 wherein the ratio of total polyol in the antiperspirant/deodorant composition to total metal salt mole ratio is 0.01:1–0.3:1.

8. An antiperspirant or deodorant composition according to claim 1 wherein the ratio of total polyol in the antiperspirant/deodorant composition to total metal salt mole ratio is 0.01:1–0.2:1.

9. An antiperspirant or deodorant composition according to claim 1 wherein the composition is anhydrous.

10. An antiperspirant or deodorant composition according to claim 2 wherein said polyol is glycerin.

11. An antiperspirant or deodorant composition according to claim 3 wherein said polyol is glycerin.

12. An antiperspirant or deodorant composition according to claim 4 wherein said polyol is glycerin.

13. An antiperspirant or deodorant composition according to claim 5 wherein said polyol is glycerin.

14. An antiperspirant or deodorant composition according to claim 6 wherein said polyol is glycerin.

15. An antiperspirant or deodorant composition according to claim 7 wherein said polyol is glycerin.

16. An antiperspirant or deodorant composition according to claim 8 wherein said polyol is glycerin.

17. An antiperspirant or deodorant composition according to claim 1 wherein the ratio of total polyol in the antiperspirant/deodorant active to total metal salt mole ratio is 0.01:1–0.5:1.

18. An antiperspirant or deodorant composition according to claim 1 wherein the ratio of total polyol in the antiperspirant/deodorant active to total metal salt mole ratio is 0.01:1–0.4:1.

19. An antiperspirant or deodorant composition according to claim 1 wherein the ratio of total polyol in the antiperspirant/deodorant active to total metal salt mole ratio is 0.01:1–0.3:1.

20. An antiperspirant or deodorant composition according to claim 1 wherein the ratio of total polyol in the antiperspirant/deodorant active to total metal salt mole ratio is 0.01:1–0.2:1.

* * * * *